(12) United States Patent
Roggenbuck

(10) Patent No.: US 8,835,122 B2
(45) Date of Patent: Sep. 16, 2014

(54) METHODS AND SYSTEM FOR THE AUTOMATED DETERMINATION OF IMMUNOFLUORESCENT FOCI USING A CELL-BASED IMMUNOFLUORESCENCE ASSAY USING SYNTHETIC CALIBRATION PARTICLES

(75) Inventor: Dirk Roggenbuck, Strausberg (DE)

(73) Assignees: Medipan GmbH, Dahlewitz (DE); Dirk Roggenbuck, Strausberg (DE)

( * ) Notice: Subject to any disclaimer, the term of this patent is extended or adjusted under 35 U.S.C. 154(b) by 0 days.

(21) Appl. No.: 14/124,660

(22) PCT Filed: Jun. 4, 2012

(86) PCT No.: PCT/EP2012/060499
§ 371 (c)(1),
(2), (4) Date: Jan. 23, 2014

(87) PCT Pub. No.: WO2012/168184
PCT Pub. Date: Dec. 13, 2012

(65) Prior Publication Data
US 2014/0162280 A1 Jun. 12, 2014

(30) Foreign Application Priority Data
Jun. 6, 2011 (EP) .................................. 11168799

(51) Int. Cl.
G01N 33/53 (2006.01)
G01N 31/00 (2006.01)
G01N 33/569 (2006.01)
G01N 33/543 (2006.01)

(52) U.S. Cl.
CPC .... G01N 33/56972 (2013.01); G01N 33/54346 (2013.01); G01N 33/5308 (2013.01)

USPC .......... 435/7.21; 435/7.1; 436/501; 436/518; 424/9.1; 424/520; 422/430; 530/300; 530/350

(58) Field of Classification Search
CPC ............ C07K 14/415; C07K 2299/00; C12N 15/8261; C12N 15/8271
See application file for complete search history.

(56) References Cited

U.S. PATENT DOCUMENTS

2003/0049866 A1    3/2003  Bushway et al.

OTHER PUBLICATIONS

Dzyubachyk, O. et al. 2010 "Automated analysis of time-lapse fluorescence microscopy images: from live cell images to intracellular foci" *Bioinformatics* 26: 2424-2430.
Ersoy, I. et al. 2009 "Segmentation and Classification of Cell Cycle Phases in Fluorescence Imaging" *Med Image Comput Comput Assist Interv* 5257: 617-624.
Parvin, B. et al. 2007 "Iterative Voting for Inference of Structural Saliency and Characterization of Subcellular Events" *IEEE Transactions on Image Processing* 16: 615-623.
Qvarnstrom O.F. et al. 2004 "DNA double strand break quantification in skin biopsies" *J European Society for Therapeutic Radiology and Oncology* 72: 311-317.
Schwartz, A. et al. 2004 "Formalization of the MESF Unit of Fluorescence Intensity" *Cytometry Part B (Clinical Cytometry)* 57B:1-6.

Primary Examiner — Lisa Cook
(74) Attorney, Agent, or Firm — Knobbe, Martens Olson & Bear, LLP

(57) ABSTRACT

The invention relates to a method for automated determination of immunofluorescent foci by means of an immunofluorescence assay using synthetic calibration particles, in addition to a system and kit for carrying out the method. In a preferred embodiment the method is characterized in that the immunofluorescent foci are gamma H2Ax foci.

20 Claims, 5 Drawing Sheets

METHODS AND SYSTEM FOR THE AUTOMATED DETERMINATION OF IMMUNOFLUORESCENT FOCI USING A CELL-BASED IMMUNOFLUORESCENCE ASSAY USING SYNTHETIC CALIBRATION PARTICLES

The invention relates to a method for automated determination of cellular immunofluorescent foci by means of an immunofluorescence assay, comprising providing a mixture of cells to be analysed and synthetic calibration particles, whereby cells and particles are fixed to a solid phase, detection of synthetic calibration particles, followed by calibration and focusing of a fluorescent microscopy device and automated evaluation system based on detection of the synthetic calibration particles, incubation of said mixture with one or more antibodies that bind to a target substrate of the cells, detection of antibodies bound to said substrates via said fluorescent microscopy device, and determination of immunofluorescent foci from image data generated by said fluorescent microscopy device using said automated evaluation system. In a preferred embodiment the method is characterized in that the immunofluorescent foci are gamma H2Ax foci.

BACKGROUND OF THE INVENTION

Standardization and automization of immunofluorescent analysis across different laboratories using different immunofluorescent equipment and methods represents a significant challenge in the field of bio-assays and diagnostics. The highly sensitive and selective detection and evaluation of fluorescence signals, especially in cell based assays, has lead to the development of fluorescence assays as some of the most important detection methods used in bioanalytics and diagnostics. The advantages of fluorescence detection, for example using fluorescence microscopy, relate to a high sensitivity of detection, relatively simple methods using fluorescence marking of the target objects in cells and the possibility of running parallel analyses of multiple parameters, whereby multiple markings of different target objects with different markers are used. This method therefore replaces more complicated methods such as absorption measurement and complicated and problematic radioactive measurements.

The manual determination and evaluation of indirect immunofluorescence tests (IIF) are however subject to various subjective factors and are additionally influenced by device-specific technical parameters. In addition to the commonly used cell substrates and reagents, microscope technology comprises of fluorescence filters, objectives, light sources, and analysis of the fluorescence patterns to be investigated, whereby each of these factors requires standardization in order to provide reliable and comparable results, especially when considering comparisons between different laboratories with different microscopic equipment and methods.

One example of an immunofluorescence assay that shows strong analytical promise for the health industry, but lacks sufficient standardisation and/or automation between different laboratories is the analysis of DNA damage via detection of DNA double strand breaks (DSBs), of which gamma H2Ax is a known marker.

DNA represents a polymer comprising mononucleotides, which themselves comprise of a base, a deoxyribose sugar and a phosphate group. Nuclear DNA is the universal carrier for genetic information. In the cell nucleus the DNA forms a complex structure with histone proteins, which are present in the form of nucleosomes, which enable the control of various nuclear processes due to the structural arrangement of chromatin. For example, during cell division particular morphological changes occur in chromatin, which allow the formation of condensed chromosomes, which are subsequently essential for reliable chromosome separation to daughter cells. Replication and transcription of DNA are regulated by a complex system of enzymes that must also interact with chromatin in order to carry out their function, which represents the basis for maintaining cellular metabolism. It is essential that the DNA molecule itself and the information coded within remains stable throughout various cellular and nuclear processes, such as transcription, replication and cell division to name but a few.

The DNA of a cell is currently under either direct or indirect influence of various metabolic processes, which can potentially modify the molecular structure of the DNA. Some changes in the structure of DNA are essential for the maintenance or enablement of DNA function, for example the appearance of transient strand breaks during development of antibody producing cells or shortly after replication when individual bases are methylated.

The overwhelming number of such changes, such as for example DSBs, are however not to be seen as important or intended events, but rather as the cause of mutation that is potentially dangerous for the entire organism. Damages to DNA can occur via exogenous processes, for example through ionization, ultraviolet radiation or through mutagenic chemicals, in addition to endogenous processes, for example through metabolic products such as free radicals.

Ionizing radiation can lead to a number of damaging effects in humans, whereby DNA DSBs are one of the most important (1-3). The effect of Ionizing radiation of living tissue is based on the transfer of energy onto the cells, whereby the extent of cell damage depends on multiple factors. Of most importance are the radiation physical properties of the radio nucleides, the absorbed doses, the duration of exposure, the radiation sensitivity of the biological system, the regional energy deposition in addition to the energy density of the radiation (linear energy transfer, LET) (4-7). The survival of a cell depends on the integrity of its DNA, whereby the eradication of malignant cells can occur due to extensive damage to the DNA. As a result of the physical processes a number of chemical changes occur to the DNA, which lead to damage to the DNA and therefore to mutation and potentially death of the cell (8, 9). The most biologically relevant damage in this sense relates to DSBs and single-strand breaks (SSB) of the DNA.

In eukaryotic cells DNA is highly condensed and localized in chromatin structure, whereby the fundamental element of chromatin is the nucleosome, which comprises of 146 DNA base pairs that are wound 1.7 times around the protein core (histone octamer). The protein core of the nucleosome is built of an octamer, which comprises of two of each of the histones H2A, H2B, H3 and H4. Each nucleosome is furthermore bound with an H1 histone, which binds the DNA linking adjacent nucleosomes. Modification of the histones, such as acetylation, deacetylation or phosphorylation, modifies the local chromatin structure and therefore plays a role in the regulation of various nuclear functions, such as replication, transcription or DNA repair.

One example of a histone modification after a DSB is the phosphorylation of histone H2Ax on serine 139. H2Ax that has been phosphorylated on serine 139 is commonly referred to as gamma H2Ax. H2Ax makes up approximately 10% of the H2A population with in chromatin and appears to be evenly distributed. If a DSB occurs then within a few minutes the H2Ax proteins are phosphorylated to form gamma H2Ax.

The phosphorylation occurs via protein kinases (ataxia telangiectasia mutated protein (ATM), DNA-dependent protein kinase (DNAPK), ataxia telangiectasia and RAD 3-related protein (ATR) (10-12). The phosphorylation is initiated in the immediate region of the DSB and extends from there, so that eventually H2Ax molecules up to a few megabases from the DSB itself are phosphorylated. The nuclear complexes that can be detected as foci relate to protein complexes that comprise of gamma H2Ax, repair proteins and proteins that function as check point control proteins for the cell cycle.

DNA double-strand breaks can be quantified using a number of methods such as pulse field gel electrophoresis, the comet assay or the tunnel assay. All of these methods exhibit however a relatively low sensitivity, which allows the determination of only a few DSBs per cell. In regards to the comet assay, the threshold at which DSBs can be reliably be distinguished from background lies at radiation doses of approximately 4 Gy. At this radiation dose there are approximately 160 DNA DSBs registered.

Through immunochemical studies it has been shown that quantification of DNA DSBs through measurement of gamma H2Ax foci using immunofluorescence is possible (13). Using this method the number of detectable foci after radiation with heavy ions and after radiation of ionizing photon radiation is proportional to the expected number and expected location of DNA DSBs. This method of quantification of DNA DSBs is sensitive enough so that DNA DSBs can be measured in the micro Gy range. The quantification of foci through staining for serine 139 phosphorylated histone H2Ax (gamma H2Ax) using immunofluorescence represents a relatively new and sensitive method for quantifying a number of DNA DSBs after the effect of ionizing radiation.

The majority of all experiments involving DSB detection using gamma H2Ax involve immunocyto-chemical experiments and evaluation and/or analysis using fluorescence microscopy. Through this approach human mononuclear cells from patients, in addition to cells arising from experimental cell lines, have been tested after being exposed to ionizing radiation. However, the method or determining gamma H2Ax foci using immunofluorescence microscopy is still relatively time consuming, subject to differences in user preferences and technical equipment and is in general a subjective analytical method (14). For the detection of gamma H2Ax foci only manual microscopic approaches have been previously used.

Description of pattern recognition of gamma H2Ax foci using intelligent software algorithms is currently limited to a few academic studies (14, 15). These studies demonstrate the possibility of automatic detection and evaluation of gamma H2Ax foci. However, there exists at the present time no evidence for adapting such algorithms for the automated evaluation of gamma H2Ax foci using commercial setups. Foci (points of light) in the cell must be counted (from 0 to 40) and the results verified through a significant number of tested cells (100 cells per slide). The current developments in immunofluorescent screening are moving towards modular, flexible and compact systems that can be individually configured, which allow the standardization of measurements. Automated interpretation systems, such as AKLIDES, represent fluorescence optical measurement systems that can detect fluorescent signals in a sensitive and meaningful manner. Such systems comprise of motorized inverse fluorescent microscopes, digital cameras, motorized xy-tables, and computers with suitable software for evaluation and analysis. The object to be detected, such as beads or cell structures, can be automatically recognized and described using digital image processing algorithms in a standardized way.

Until now there has been no satisfactory experience or reports as to whether pattern recognition of gamma H2Ax foci using an automatic detection system can be obtained (16). The complications surrounding the automatic pattern recognition of gamma H2Ax foci relates to the complex structures of cell based assays in addition to the complex immunofluorescence patterns generated through such analysis. Furthermore, the calibration, which is of fundamental importance for the standardization of the method, has not been clarified. There exists a serious need for appropriate calibration reagents, which enable the determination and analysis of H2Ax foci using an automated interpretation system.

The technical problem in calibrating gamma H2Ax detection lies in the diversity of immunofluorescence images, which are used for quantification of a signal. Of significant importance is the presence of overlap and layover between separate gamma H2Ax foci. These effects can create significant problems in quantification. Furthermore, the various and differing properties of cell based tests in the systems used to analyse gamma H2Ax foci represent a serious challenge to standardization of the procedure (17, 18).

Automatic microscopic interpretation systems can be standardized using technical components of the analysis system, such as calibrations agents (for example synthetic micropartides), as are commonly used in flow through cytometry.

An intelligent algorithm, which is used for such automatic standardization, is defined by the determining guidelines that it provides (19-21). Automated objective methods are well suited for such standardization, through their exclusion of subjective influencing factors. In this sense, self-learning systems appear upon first inspection to be technically suitable. However, after closer examination it appears that self-learning systems are in fact not suitable for the standardization of the analysis of gamma H2Ax foci. The world wide distribution of devices with self-learning software (especially software that could modify known patterns and also receive input from users regarding new patterns) would improve the individual classification success of each individual laboratory. However, the present situation is that each individual self-learning system tends to develop away from one another, so that the learning processes tend to move further and further away from the original data provided in the system (20, 21). The consequence of this is that self-learning systems provide local (laboratory-specific) improvements without enhancing common inter-laboratory standardization.

A world wide classification standard for gamma H2Ax foci is therefore only possible with a statistically defined method using standardized analytical reference reagents, such as microparticles, to calibrate the method, which then provides a basis for automated optical interpretation.

SUMMARY OF THE INVENTION

By incorporating standardised reagents and methods an analytical platform can be established that is compatible with different technical setups throughout the world. Differences in technical setups relate to different microscope setups, different methods of generating fluorescence or different software setups for detecting fluorescent foci. A standardised approach overcomes these differences and ultimately enables accurate and reliable measurement of fluorescent foci in biological samples. This subsequently enables, in one aspect of the invention, an enhanced accuracy in diagnosis of disease, such as diseases represented by modified numbers of immunofluorescent foci, for example increased numbers of DNA double strand breaks.

When measurements of fluorescent foci are indicative of disease as markers, and a standardised approach is used on a large scale in to investigate such markers, the reliability of the analysis and diagnosis is increased enormously. Additionally, the data can over time be compiled, leading to the large data sets available for further diagnoses. Only through standardised approaches can automated diagnoses be improved in accuracy, which requires novel methods than can be reliably applied on different microscopic setups, leading to the comparable quantifiable results. At the present time no reliable approaches for standardised assessment of fluorescent foci numbers have been described in the prior art, which are suitable for the analysis of biological samples as described herein.

In light of the prior art the technical problem underlying the present invention is to provide a method for objective automated determination of immunofluorescent foci by means of an immunofluorescence assay.

This problem is solved by the features of the independent claims. Preferred embodiments of the present invention are provided by the dependent claims.

Therefore, an object of the invention is to provide a method for automated determination of cellular immunofluorescent foci by means of an immunofluorescence assay, comprising:
  a. providing a mixture of cells to be analysed and synthetic calibration particles, whereby cells and particles are fixed to a solid phase,
  b. detection of synthetic calibration particles, followed by calibration and focusing of a fluorescent microscopy device and automated evaluation system based on detection of the synthetic calibration particles,
  c. incubation of said mixture with one or more antibodies that bind to a target substrate of the cells,
  d. detection of antibodies bound to said substrates via said fluorescent microscopy device, and
  e. determination of immunofluorescent foci from image data generated by said fluorescent microscopy device using said automated evaluation system.

The invention can be used for the automated determination of any cellular immunofluorescent foci arising in fluorescence microscopy. In a preferred embodiment the method is characterized in that said immunofluorescent foci are gamma H2Ax foci. H2Ax foci are particularly suited to analysis and/or determination with the method of the present invention due to their size and other visual and physical characteristics within the cell nucleus. Due to the size of H2Ax foci, quantification can become very difficult, in light of potentially overlapping foci of clustered spatial distribution within the nucleus. The present invention solves this problem and enables reliable automated quantitative analysis of H2Ax foci, which represents a surprising and advantageous development over those methods previously known.

In a preferred embodiment the method is characterized in that said synthetic calibration particles are microparticles, preferably between 1-100 μm in diameter. The particle range of 1-100 μm in diameter includes particles of approximately 1, 10, 20, 30, 40, 50, 60, 70, 80, 90, or 100 μm in diameter, and any value falling within the range. Particles may however be of any size, as long as said particles are suitable for focusing and calibrating said microscopy system. Particles of this particular size (1-100 μm in diameter) are surprisingly advantageous, as they provide an appropriate calibration of the microscopy device regardless of the foci size to be analysed. H2Ax foci can be reliably analysed using a system calibrated with particles of this size, in addition to either larger or smaller foci.

In one embodiment the method is characterized in that said synthetic calibration particles and/or antibodies are specifically marked using fluorescent markers. In a preferred embodiment the particles are already marked with fluorescent reagent before the method or system is initiated. The particles can also be marked using fluorescently marked antibodies or other such means, so that particles can be detected and measured for calibration. Separate antibodies that bind either particles or the cell substrate corresponding to the foci, each exhibiting different fluorescent markings, may be co-incubated with the cells and particles on the solid phase surface before calibration, if required. Physical or other characteristics of the particles may also be used for detecting the particles and subsequent calibration, such as shape, colour or reflective properties, so that the calibration and focusing of the microscopy device is not dependent on fluorescence, rather on detection of the particles using any means suitable.

In a preferred embodiment the method is characterized in that said antibodies relate to one or more primary antibody that binds to the target substrate of the cell, and one or more secondary antibody that is fluorescently marked and binds to the primary antibody, thereby facilitating detection of the bound substrate as immunofluorescent foci.

In one embodiment the method is characterized in that said cells are selected from mononuclear blood cells, such as lymphocytes, monocytes and/or macrophages, in-vitro cultured cells such as fibroblasts, or cells from an experimental cell line. The analysis of cells obtained from blood, or the other cells described herein, provides the unexpected advantage that the cells can be easily and reliably fixed quickly to the solid phase for analysis, so that in combination with the particles, the objects to be analysed are in a fixed position, therefore enabling reliable quantification.

In a preferred embodiment the method is characterized in that said calibration in step b) or said determination in step e) comprises additionally of detecting and locating of cells via detection of stained or marked cell nuclei, preferably via detection of DAPI-stained cell nuclei. Other staining can be used for detecting DNA and therefore determining cell nucleus position, such as Hoechst staining, or other DNA-binding or -identifying reagents. In a preferred embodiment the method is characterized in that said determination provides determination of foci number per cell. Calculation of foci per cell ultimately provides information in an automated analysis that allows comparison to other data sets. Such quantification can be used for diagnosis of any given disease that is associated with a quantitative change in foci number.

In one embodiment the method is characterized in that said automated evaluation system of step e) comprises a computing device with a computer readable memory storing executable instructions as software, comprising of modules that when executed by the computer perform functions of autofocus control, automated image acquisition, automated image analysis and/or automated pattern recognition. The evaluation system allows analysis and computation of foci number on the basis of the image data generated by the microscopy device. In order to carry out this evaluation and determination of foci number, images are automatically analysed for shape, size and intensity of individual foci. The rules for identifying foci are therefore embodied in computer programmes which are run on the computing device of the evaluation system.

In one embodiment the method is characterized in that the focusing of the fluorescent microscopy device and automated evaluation system occurs via dynamic auto-focusing of the microscopic image.

The invention further relates to the use of the method as described herein for determining the number of DNA double strand breaks in a cell and/or cell population, whereby the number of gamma H2Ax foci is proportional to the number of DNA double strand breaks. As described above, the relationship and biological mechanism underlying H2Ax formation in the context of DNA damage is understood. A method for reliable automated quantification of such foci is however not yet available.

The invention relates furthermore to the use as described herein for determining DNA damage in a cell and/or cell population, whereby
   a. the number of gamma H2Ax foci in test cells is compared to the number of gamma H2Ax foci in control cells, and
   b. a larger number of gamma H2Ax foci per cell in the test cells in comparison to the control cells indicates increased DNA damage in the test cells.

In a preferred embodiment the method as described herein is applied for determining radiation exposure of a cell and/or cell population to ionizing or any other kind of radiation, or any other DNA-damaging substance or treatment. Using a method as described herein, quantitative information is obtained on DNA damage that has occurred in cells or cell populations, thereby providing insights into mechanisms underlying disease, or for identifying disease, for example when using the method in a diagnostic application for identifying cancer or cancer-risk patients.

Using gamma H2Ax detection to determine the extent of DSB induction may help to detect precancerous cells, to stage cancers, to monitor the effectiveness of cancer therapies and to develop novel anticancer drugs.

The invention further relates to a system for the automated determination of immunofluorescent foci by means of an immunofluorescence assay according to the method as described herein, comprising
   a. a mixture of cells to be analysed and synthetic calibration particles, whereby cells and particles are fixed to a solid phase
   b. a fluorescent microscopy device comprising a fluorescent microscope with a camera, a motorized scanning stage and multichannel light-emitting diodes (LED), and
   c. an automated evaluation system comprising a computing device with a computer readable memory storing executable instructions as software, comprising of modules that when executed by the computer perform functions of autofocus control, automated image acquisition, automated image analysis and/or automated pattern recognition,
      whereby two or more colour channels are analysed, each corresponding to either synthetic calibration particles or target substrate-associated immunofluorescent foci.

The system of the present invention was developed specifically for carrying out the method as described herein. The system comprises components that are directly and specifically related to the method, thereby forming a unified invention. The contents of the system and those reagents applied in the method as described represent unique contributions to the prior art, thus justifying the unity of the invention. The invention also relates to a kit, which was developed explicitly for carrying out the method of the invention. As for the system, the kit comprises contents that are tailored for the present invention (for example slides with fixed particles), therefore representing one aspect of a unified invention.

The invention therefore further relates to a kit for carrying out a method for automated determination of immunofluorescent foci by means of an immunofluorescence assay according to the method as described herein, comprising a. One or more solid phases comprising synthetic calibration particles fixed to the surface of said solid phase, upon which the cells to be analysed are to be fixed,
   b. One or more conjugates comprising an immunoglobulin-specific antibody conjugated with a fluorescent label, preferably for use as a secondary antibody, and optionally
   c. wash buffer, cover slips, covering medium, and/or fluorescent labels for the synthetic calibration particles, primary antibody and/or secondary antibody.

DETAILED DESCRIPTION OF THE INVENTION

The synthetic calibration particles relate to microparticles, beads or carriers of any substance or material, for example those that are known in the art that are suitable for the method of the present invention, for example microparticles, particles or beads composed of natural or artificial polymers, sepharose, cellulose, glass or metal oxides. The calibration particles are capable of being marked with fluorescent markers or are preferably already fluorescent, so that an additional fluorescent marking is not required. Fluorescent markings may refer to those commonly known in the art, such as fluorescent proteins, such as GFP, or rhodamine, fluorescein or derivatives thereof, such as FITC, TRITC, or any kind of suitable fluorophore.

The target substrate to be detected relates to a cellular structure of a spatial distribution within and/or on the cell that results in immunofluorescent foci formation after antibody binding and/or detection.

The cellular immunofluorescent foci of the present invention are therefore any immunofluorescent image object(s) that is sufficiently distinct for detection as a point of immunofluorescence, of any diameter or shape, characterised in that it is distinguishable from the background of the image. Foci size, shape or other visual characteristics can also be measured and incorporated into the analysis of the method of the present invention.

The term "automated" refers to a process that is carried out to some extent, preferably to a large extent, or entirely, without direct intervention of a user, thereby relieving the system and/or method from subjective user-dependent influence.

An immunofluorescence assay is any assay involving antibody binding or interaction, or binding of an antibody-like molecule, such as an antibody-fragment or non-antibody peptide, to a substrate of interest and subsequent detection of said interaction based on fluorescence.

The mixture of cells to be analysed and synthetic calibration particles relates to a mixture in any proportion. The number of calibration particles must only be sufficient so that the microscope can detect them and perform the calibration and focusing. There may be more particles than cells or more cells than particles on the solid phase surface.

The term "fixed" or "immobilized" relates to any means of binding or attaching the cells to the solid phase. Principally the fixing refers to physical restriction of the particles and cells, so a reliable quantification can be carried out, even if the microscope takes various images from across various regions of the solid phase.

The term "solid phase" relates preferably to a slide, but can relate to any solid phase that provides a surface for analysis of the particles and cells. Microscope slides of glass or synthetic material can be used, such as plastic, as can any micro-titer plate or other well-like structure that may be subject to fixing of microparticles and cells. The terms solid phase, slide or analysis surface may be used interchangeably throughout the application.

The "detection" of synthetic calibration particles relates primarily to a measurement of their size, shape or intensity of light or fluorescence of the particle. Any property of the particle can be used for detection and subsequent calibration and focusing, as long as the property allows detection using the microscopic device of the present invention.

Calibration of the microscopy device and/or evaluation system refers to any necessary modifications to the device setup as are deemed necessary for optimal image acquisition. Focusing and calibration can be understood as a single procedure involving focusing of the microscopic image, which is optionally complemented by additional adjustments in microscopy parameters that are preferred for obtaining suitable image data. Such calibration measures are known to one skilled in the art of microscopy.

Focusing of the microscopy device relates to focusing as understood by one skilled in the art, in order to obtain clear images. One example, as used in the examples below, is calculation of the point spread function (PSF) via deconvolution of the microparticles of the sample, and the PSF is subsequently used for analysis of the foci. When the particles are brought into appropriate focus, the analysis of the immunofluorescent foci can be carried out automatically, The fluorescent microscopy device and automated evaluation system are typically microscopy devices as commonly used in the field and computer-based evaluation systems capable of carrying out software-based algorithms for detection and analysis of image data. Examples are provided below.

FIGURES

The invention is further described by the figures. These are not intended to limit the scope of the invention.

EXAMPLES

Figure 1:
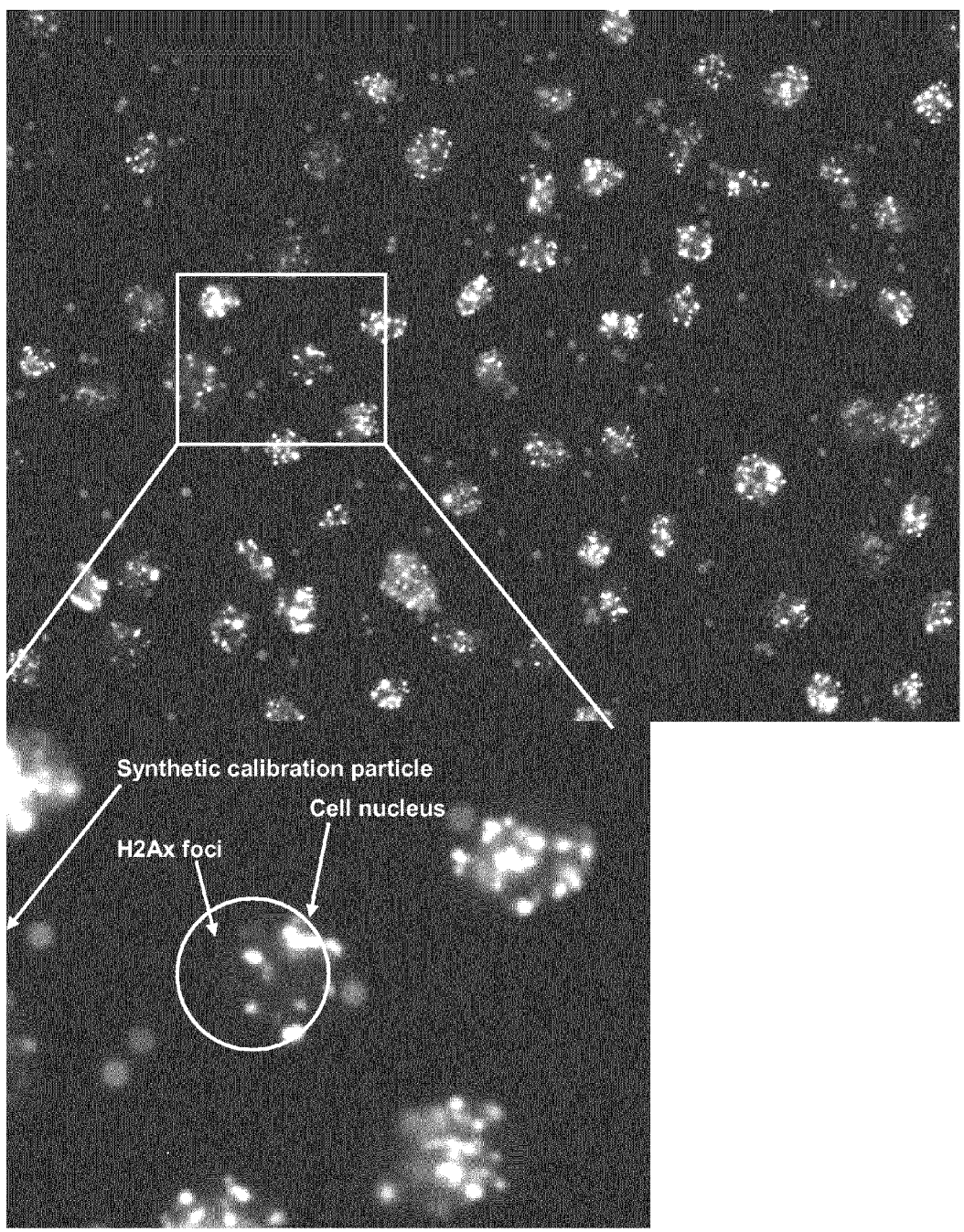
FIG. 1: Immunofluorescence image capture of gamma H2Ax foci in fixed irradiated cells on a slide with calibration microparticles.

The invention is further described by the following examples. These are not intended to limit the scope of the invention. The methods described herein were used in carrying out the present invention as demonstrated in the examples. They are intended to further describe the invention by way of practical example and do not represent a limiting description of the invention.

Example 1

Demonstration of the Method Described Herein for Automated Determination of Immunofluorescent Foci by Means of an Immunofluorescence Assay Using Synthetic Calibration Particles Immobilization of the Calibration Microparticles on Slides Glass slides were coated with 10 µl per application spot of poly-lysine (Sigma, 5 µg/ml) were incubated for 4 hours in a moist incubation chamber. After rinsing the non bound poly-lysine from the slides using PBS, 10 µl of the calibration microparticle suspension (6000 calibration microparticles per application spot) were pipetted to the moist application spots. This suspension was subsequently dried under a sterile hood and allowed to rest on the slide overnight.

Preparation of Lymphocyte Suspension for the Detection of DSB in Peripheral Mononuclear Blood Cells The blood sample of a test subject was inverted two times. 3 ml of uncoagulated blood (ratio 1:1) was pipetted onto the separation membrane of a centrifugation tube and subsequently centrifuged at 1000×g for 10 minutes at room temperature without braking. The band of mononuclear blood cells was carefully taken up using a 1000 µl pipette, and subsequently transferred to a new centrifuge tube and left on ice.

All further steps were carried out on ice or centrifugation was carried at 4° C. Mononuclear blood cells were mixed with the same volume of PBS and the tube was inverted 3-4 times in order to mix the solution. The mixture was subsequently centrifuged at 300×g (1400 rpm) for 10 minutes. The supernatant was removed using vacuum pump and a pipette tip. The pellet was subsequently resuspended using 9 ml of distilled water, incubated for 12 seconds at room temperature and subsequently mixed with one ml of cold 10×PBS buffer. The entire procedure was repeated twice.

Fixing of Cells to the Slide with Immobilized Calibration Microparticles

After determination of the number of cells in the purified cell suspension (via a counter chamber) 150,000 cells were seeded onto each application spot of the slide comprising immobilized calibration microparticles. The corresponding volume of the cell suspension was pipetted onto an autoclaved glass dish and filled to the necessary volume with culture medium. 50 µl of the mixed suspension is then transferred to the application spots of the slide, which are incubated for one hour at room temperature.

For the seeding of cells from experimental cell lines, which have previously been treated with radioactive substances (for example $^{188}$Re-perrhenate), 70,000 cells were used per application spot. After provision of the according volume of suspension the cells on the slide are sedimented in a cyto-centrifuge for 3 minutes at 250 U/min.

The fixation of the cells occurs in a staining tray with 1% formaldehyde for 15 minutes at room temperature. After fixation the slides are washed three times for 5 minutes in a PBS bath whilst being gently shaken. For permeabilization of the mobilized cells the slides were incubated three times for 5 minutes with a 1% triton-X100/PBS solution. Subsequently the slides are washed three times in a PBS bath being gently shaken. To block the free binding sides the slides are placed in an incubation chamber and subsequently dried. After drying, 25 µl of a 1% PBS-BSA-solution is applied to each application spot and incubated for 30 minutes.

Immunofluorescence Staining

The slides covered with cells are placed in an incubation chamber and 25 µl of primary antibody is applied to each application spot (dilution 1:1000 in PBS/BSA 1%) and is incubated for one hour at room temperature. Subsequently the slides are carefully rinsed using a rinse bottle with PBS solution and thereafter washed three times for 5 minutes in PBS with gentle shaking. Afterwards, 25 µl of the fluorescence labelled secondary antibody (dilution 1:1000 PBS/BSA 1%) is pipetted to the application spot and covered. The slides are subsequently incubated for one hour at room temperature. The slides are again washed after incubation. For the automatic interpretation of slides on the AKLIDES system a covering medium is applied to every application spot and a cover slip is carefully mounted. For an example image see FIG. 1.

Automated Standardized Interpretation of Cells Via Calibration Microparticles Using the AKLIDES System The technical basis of the AKLIDES system relates to the inverse motorized fluorescent microscopes IX81 (Olympus, Japan), which can be completely controlled via the AKLIDES software. Through the combination of a motorized xy table (IM120, Märzhäuser, Wetzlar), a sensitive grey-scale camera for fluorescent images (PS4, Kappa, Gleichen) and a controllable light emitting diode as a light source (LED) (PrecisExcite, CoolLed, UK) the automated capture and processing of fluorescence tests is enabled. Various slides or plates can be used as sample carriers, the slides comprising of various formats (1, 6, 12, 18 wells) in addition to micro-titer plates (24, 48, 96, 384, 1532 wells). The specially developed software controls the interaction of the components and takes over the automatic focusing and quality control of the test. Captured image data is then directly, during the measurement, evaluated using the image analysis algorithms. Using objectives of different sizes (from 1.25× to 60×) and high transmission fluorescence filters (in a spectrum of 350-700 nm) a vast numbers of tests and fluorescence subjects can be analyzed and/or combined.

Figure 2:
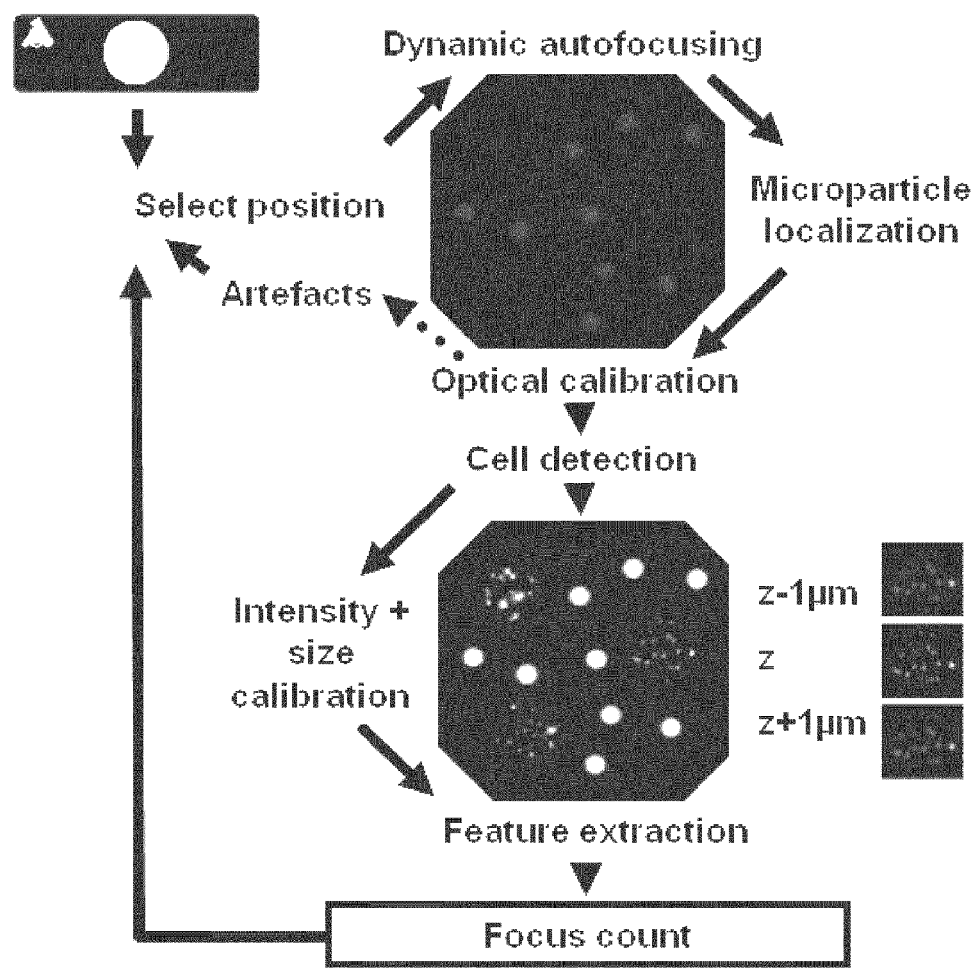
FIG. 2: Schematic representation of the automated gamma H2Ax measurement using standardized microparticles.

See FIG. 2 for a schematic representation of the automated gamma H2Ax measurement.

The microparticles with standardized size and brightness (unit: MESF-molecules of equivalent soluble fluorochrome, source: Schwartz 2004) are used at the beginning of the measurement for focusing.

Use of the microparticles for focusing represents a very high focus quality which is independent of the cell line used. Artefacts can be identified and easily excluded from analysis. Additionally, the entire optical path in the detection wave length is calibrated. The point spread function (PSF) is calculated via deconvolution of the microparticles of the sample, and the PSF subsequently used for analysis of the gamma H2Ax foci. The precision of the measurement is increased through this calibration step because light outside of the focal plane can be calculated through knowledge of the PSF.

Figure 3:
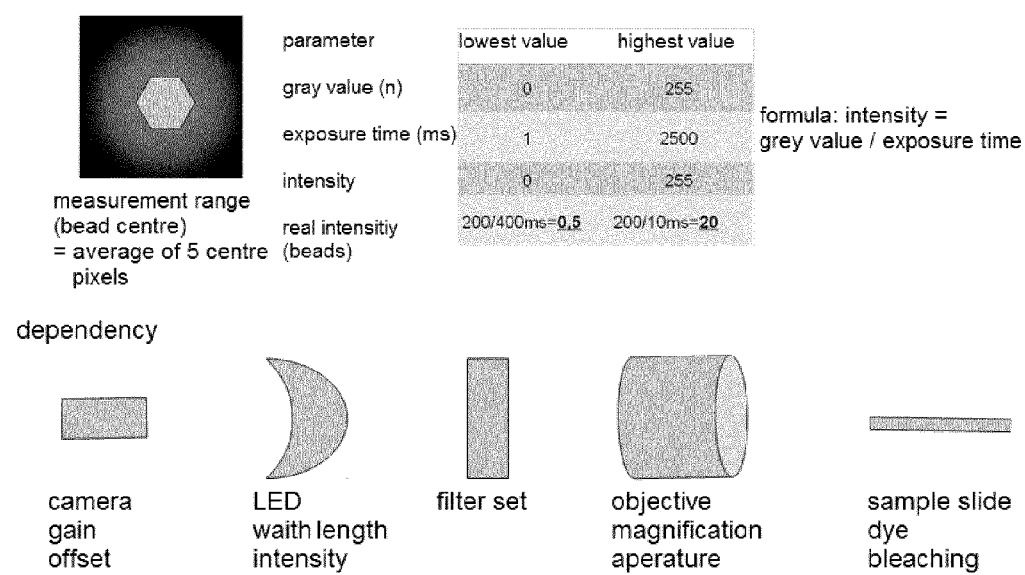
FIG. 3: Principal of the intensity measurement of the microparticles in consideration of the complex dependencies of the fluorescence intensity measured in the detector.

Measurement of the foci occurs in a second detection channel, in which the particles are used for the intensity and size calibration. FIG. 3 shows the detection principal and the calculation of intensity. The microparticles are detected due to their size and shape characteristics and the intensity of the microparticle is measured from its centre. A standardized analysis of gamma H2Ax foci through referencing the measured foci size and intensity is possible, directly in the preparation. Through this approach various optical detection methods and optical dissolutions can be compared using the calibration microparticles as described herein.

Example 2

Demonstration of the Use of the Method as Described Herein for Determining the Number of DNA Double Strand Breaks in Cells, for Determining DNA Damage or for Determining Radiation Exposure of a Cell and/or Cell Population to Ionizing or any Other Kind of Radiation Radionuclide $^{188}$Re-perrhenate ($^{188}$Re) was obtained by elution of a 40 GBq alumina based $^{188}$W/$^{188}$Re generator (ITG, München, Germany). The physical characteristics of $^{188}$Re are: physical half life 16.9 h, maximal beta energy 2.1 MeV, gamma emission 155 keV (15% abundance). The generator was eluted with 5 ml of 0.9% saline to achieve activity concentrations of about 1.0 GBq/ml of carrier free $^{188}$Re.

Cell Culture

The thyroid rat cell line PC Cl3 (Clinical Cooperation Unit Nuclear Medicine, DKFZ, Heidelberg, Germany) is a sodium iodine symporter (NIS) positive subline of the FRTL5 cell line available in the American Type Culture Collection (ATCC). The cells were routinely grown as adherent monolayer in Ham's F12 medium (Gibco Invitrogen GmbH, Darmstadt, Germany) supplemented with 5% fetal bovine serum, insulin (10 µg/ml), hydrocortison (10 nM), transferrin (5 µg/ml), somatostatin (10 ng/ml), glycin-histidin-lysin (10 ng/ml) and TSH (10 mU/ml). Exponentially growing cells were routinely split every 3 days using accutase (PAA Laboratories GmbH Cölbe, Germany). Cultures were maintained at 37° C. in a humidified 5% $CO_2$ in air atmosphere. The culture medium was renewed every 2-3 days as well as before the application of radioactivity.

Irradiation Experiments

For experiments, aliquots of 0.5×10$^6$ cells/well were seeded in six-well tissue culture plates in a volume of 2 ml/well of activity-free standard medium and were pre-cultured for two days before irradiation. To inhibit active radionuclide transport mediated by NIS, cells were preincubated with 0.4 mM final concentration of sodiumperchlorate (NaClO$_4$) which acts as competitive inhibitor for $^{188}$Re (23). After incubation with NaClO$_4$ for 10 minutes $^{188}$Re solutions were added to the cells using one well for each dose point. Activity concentrations of 5.7-57 MBq/2 ml $^{188}$Re corresponding to 0.5-5 Gy extracellular dose were employed (calculated using dose point kernels) (23,24). Irradiation was conducted for one hour at 37° C. After exposure with $^{188}$Re cells were washed with PBS and harvested by adding accutase (PAA, Coelbe, Germany). The resulting cell suspension contained about 0.5×10$^6$ cells in 1.5 ml culture medium. Immediately after irradiation the cells were processed further for gamma H2AX foci evaluation.

Immunohistochemistry and Foci Analysis

For immunostaining, irradiated cells were centrifuged onto glass slides by cytospin (Hettich Universal 30 RF, Hettich GmbH, Tuttlingen, Germany) to about 70,000 cells per spot, 250 rpm, 3 min. Subsequently, cells were fixed in 4% formalin for 15 minutes at room temperature. After fixation, cells were washed with PBS three times. To permeate cell membranes 0.1% Triton X100 was added and incubated for 5 minutes three times followed by three washing steps with PBS.

After incubation with 1% bovine serum albumin in PBS (BSA/PBS for 30 minutes. antiphospho-Histone H2A.X (Ser139), clone JBW301 (mouse, monoclonal IgG1, Millipore GmbH, Schwalbach, Germany) at a dilution of 1:800 in BSA/PBS was incubated for 1 h at room temperature. Anti-mouse IgG conjugated to Alexa Fluor 488 (Invitrogen, Karlsruhe, Germany) at 1:400 dilution was incubated for 1 h in the dark after three wash steps. In order to stain DNA, 4,6'-diamidino-2-phenylindole (DAPI, Sigma-Aldrich, Taufkirchen, Germany) was added 10 minutes after another wash cycle (3×PBS). Slides were washed again two times and mounted with fluorescent mounting medium (Dako Deutschland GmbH, Hamburg, Germany).

Automated Interpretation of Gamma H2AX Foci

The concept of the fully automated interpretation system AKLIDES for evaluation of immunofluorescence patterns like gamma H2AX foci is based on novel mathematical software algorithms for pattern recognition. Gamma H2AX foci were assessed automatically using a motorized inverse fluorescence microscope (Olympus IX81, Olympus, Japan) with a motorized scanning stage (IM120, Märzhä, Germany), 400 nm and 490 nm light-emitting diodes (LED) (PrecisExcite, CoolLED, UK) and a charge-coupled device (CCD) grey-scale camera (DX4, Kappa, Germany).

The interpretation system is controlled by the AKLIDES software (Medipan, Germany) consisting of modules for device and autofocus control, image analysis with pattern recognition algorithms. The novel autofocus based on Haralick's image characterization of objects through grey-scale transition used either DAPI as fluorescent dye or the microparticles of the present invention for focusing, quality evaluation and object recognition. Scanning algorithm of AKLIDES system sequentially selects position of slide wells and focus cell layer in DAPI channel mode.

Readjustment of camera integration time ensures correctly exposed cell nuclei. The image obtained will be subsequently evaluated for quality attributes. In case of artifacts, a new subwell position will be selected automatically. Afterwards, immunofluorescence of detected cells is captured in three z-layers. Selection of cell features for each layer and combination of features enable calculation of focus count (FIG. 2).

Technical Aspects of Automatic Gamma H2AX Foci Image Processing

Automatic image capturing process was properly performed in DAPI fluorescence channel using a 60× objective. Starting with a coarse focusing using wide z-steps (10 μm) followed by fine focusing with narrow z-steps (0.5 μm) detection of the main focal plane could be assured. To change fluorescence wavelength, the excitation wavelength was switched in combination with the dual-band filterset giving a typical switching time of 100 ms. Attaching importance to "on-the-fly" analysis of images, algorithms were selected by performance, scalability and quality of analysis. To eliminate artifacts, an additional qualitative image analysis was performed by dividing the image content into tiles of equal size with subsequent calculation of tile sharpness and homogeneity. Object segmentation was conducted by histogram-based threshold algorithm followed by watershed transformation. Both cell aggregates and heavily damaged cells were excluded by analyzing convexity of objects. Segmented nuclei were characterized by regional, topological and texture/surface descriptors. Gamma H2AX foci were quantified by counting the number of discrete foci in each cell. Definition of position for a discrete focus was a) pixel which is brighter than the eight neighbor pixels, b) minimum distance of one pixel to next focus (size of pixel: 110 nm), and c) minimal brightness (brighter than average brightness of cell). A minimum of 10 fields containing 100 cells were counted at each slide.

Figure 4:
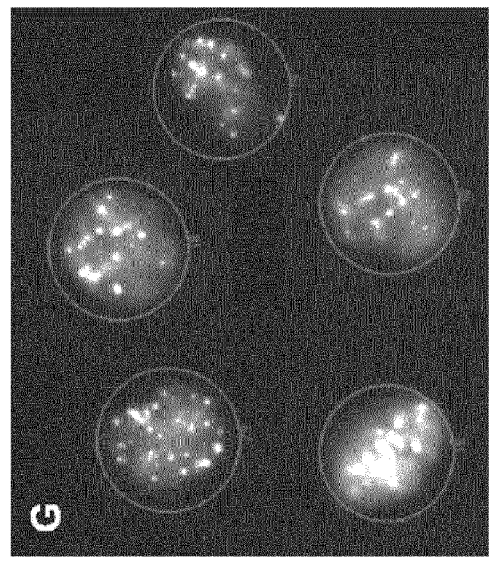
FIG. 4: Immunofluorescence staining against phosphorylated histone H2AX (gamma H2AX foci) for IR induced foci in the PC CI3 cell line 30 minutes after exposure of 0 and 1 Gy $^{188}$Re. Examples of representative images for controls (panels A-C) and after irradiation with 1 Gy (panels D-F). The photos are made by automated system AKLIDES at 60× magnification. DAPI nuclear staining (A, D), background gamma H2AX foci for controls (B) and gamma H2AX foci for irradiated cells (E) as well as merged fluorescence images (C, F). Panel G demonstrate the images of captured cells (circles) with results of digitally counted foci (dots).
Figure 4:
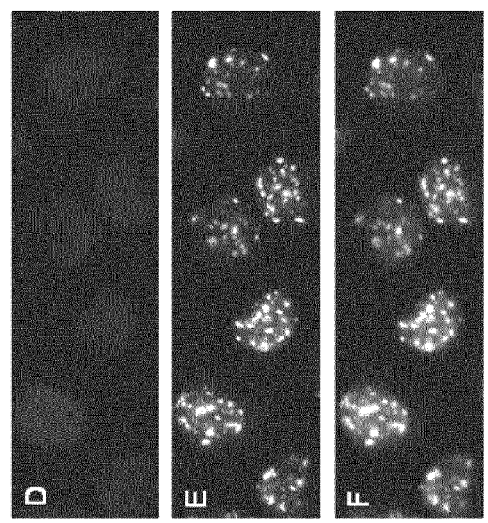
Figure 4:
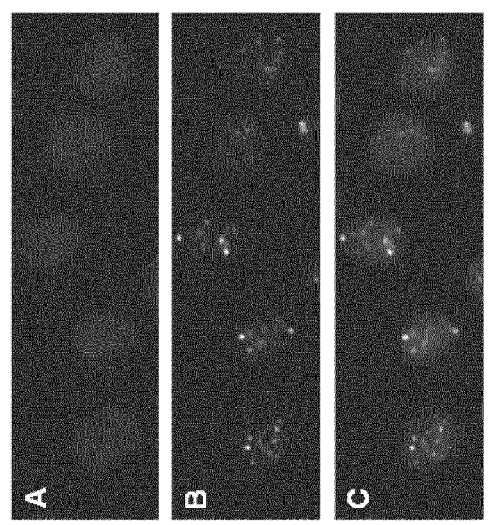

Representative images of immunofluorescence patterns by staining against gamma H2AX foci and nuclear staining for IR induced foci in PC Cl3 cells after exposure to 0 Gy and 1 Gy $^{188}$Re are shown in FIG. 4. DAPI can be used as a fluorescent dye for additional quality evaluation if required (FIG. 4A, 4D). Results of automatically counted foci are presented in FIG. 4G and FIG. 5.

Figure 5:
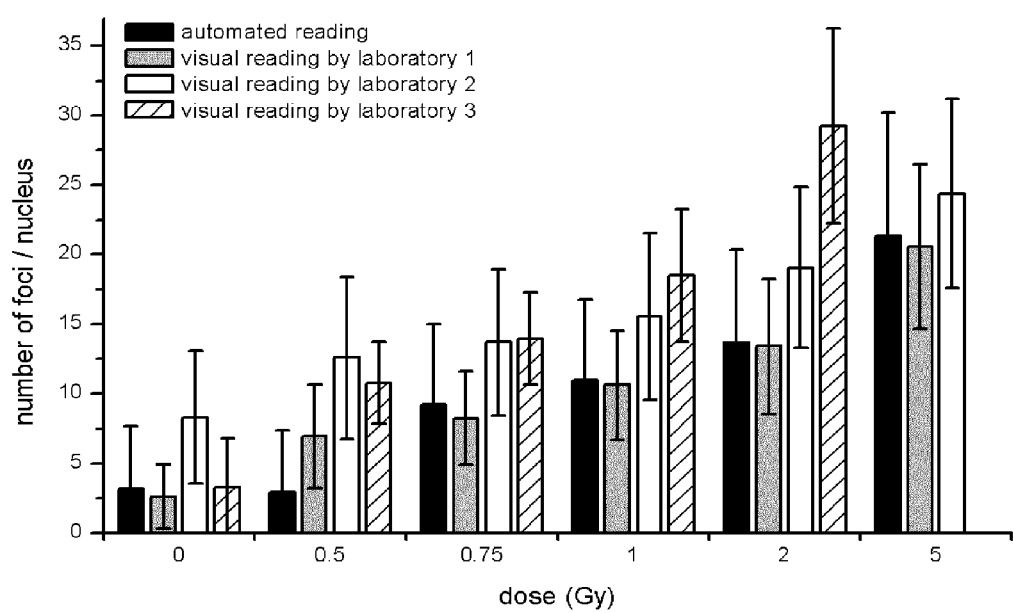
FIG. 5: Dose response curve obtained for PC CI3 cells irradiated with various doses of $^{188}$Re by digitally scored data (AKLIDES) (mean number of foci per cell±SD).

As can be seen in FIG. 5 the number of foci per nucleus increases in response to increasing radiation dose. This effect was observed when measured with the automated system as described herein, in addition to manual (visual) assessment of the number of fluorescent foci. This demonstrates the usefulness of the present automated method and system for determining the number of DNA double strand breaks in cells, for determining DNA damage or for determining radiation exposure of a cell and/or cell population to ionizing or any other kind of radiation.

Reference List

1. Olive P L, Banath J P: Phosphorylation of histone H2AX as a measure of radiosensitivity. *Int J Radiat Oncol Biol Phys* 2004, 58:331-335.
2. Banath J P, MacPhail S H, Olive P L: Radiation sensitivity, H2AX phosphorylation, and kinetics of repair of DNA strand breaks in irradiated cervical cancer cell lines. *Cancer Res* 2004, 64:7144-7149.
3. Banath J P, Fushiki M, Olive P L: Rejoining of DNA single- and double-strand breaks in human white blood cells exposed to ionizing radiation. *Int J Radiat Biol* 1998, 73:649-660.
4. Fernandez-Capetillo O, Allis C D, Nussenzweig A: Phosphorylation of histone H2B at DNA double-strand breaks. *J Exp Med* 2004, 199:1671-1677.
5. Fernandez-Capetillo O, Celeste A, Nussenzweig A: Focusing on foci: H2AX and the recruitment of DNA-damage response factors. *Cell Cycle* 2003, 2:426-427.
6. Foster H A, Bridger J M: The genome and the nucleus: a marriage made by evolution. Genome organisation and nuclear architecture. *Chromosoma* 2005, 114:212-229.
7. Frankenberg-Schwager M: Review of repair kinetics for DNA damage induced in eukaryotic cells in vitro by ionizing radiation. *Radiother Oncol* 1989, 14:307-320.
8. Lobrich M, Kiefer J: Assessing the likelihood of severe side effects in radiotherapy. *Int J Cancer* 2006, 118:2652-2656.
9. Rothkamm K, Lobrich M: Misrepair of radiation-induced DNA double-strand breaks and its relevance for tumorigenesis and cancer treatment (review). *Int J Oncol* 2002, 21:433-440.
10. Rogakou E P, Nieves-Neira W, Boon C, Pommier Y, Bonner W M: Initiation of DNA fragmentation during apoptosis induces phosphorylation of H2AX histone at serine 139. *J Biol Chem* 2000, 275:9390-9395.
11. Rogakou E P, Boon C, Redon C, Bonner W M: Megabase chromatin domains involved in DNA double-strand breaks in vivo. *J Cell Biol* 1999, 146:905-916.
12. Rogakou E P, Pilch D R, Orr A H, Ivanova V S, Bonner W M: DNA double-stranded breaks induce histone H2AX phosphorylation on serine 139. *J Biol Chem* 1998, 273: 5858-5868.
13. Klokov D, MacPhail S M, Banath J P, Byrne J P, Olive P L: Phosphorylated histone H2AX in relation to cell survival in tumor cells and xenografts exposed to single and fractionated doses of X-rays. *Radiother Oncol* 2006, 80:223-229.
14. Bocker W, Iliakis G: Computational Methods for analysis of foci: validation for radiation-induced gamma-H2AX foci in human cells. *Radiat Res* 2006, 165:113-124.

15. Hou Y N, Lavaf A, Huang D, Peters S, Huq R, Friedrich V, Rosenstein B S, Kao J: Development of an automated gamma-H2AX immunocytochemistry assay. *Radiat Res* 2009, 171:360-367.
16. Avondoglio D, Scott T, Kil W J, Sproull M, Tofilon P J, Camphausen K: High throughput evaluation of gamma-H2AX. *Radiat Oncol* 2009, 4:31.
17. Costes S V, Boissiere A, Ravani S, Romano R, Parvin B, Barcellos-Hoff M H: Imaging features that discriminate between foci induced by high- and low-LET radiation in human fibroblasts. *Radiat Res* 2006, 165:505-515.
18. Lobrich M, Rief N, Kuhne M, Heckmann M, Fleckenstein J, Rube C, Uder M: In vivo formation and repair of DNA double-strand breaks after computed tomography examinations. *Proc Natl Acad Sci USA* 2005, 102:8984-8989.
19. Hiemann R, Hilger N, Michel J, Nitschke J, Bohm A, Anderer U, Weigert M, Sack U: Automatic analysis of immunofluorescence patterns of HEp-2 cells. *Ann NY Acad Sci* 2007, 1109:358-371.
20. Hiemann R, Buttner T, Krieger T, Roggenbuck D, Sack U, Conrad K: Challenges of automated screening and differentiation of non-organ specific autoantibodies on HEp-2 cells. *Autoimmun Rev* 2009, 9:17-22.
21. Hiemann R, Hilger N, Sack U, Weigert M: Objective quality evaluation of fluorescence images to optimize automatic image acquisition. *Cytometry A* 2006, 69:182-184.

The invention claimed is:

1. Method for automated determination of cellular immunofluorescent foci by an immunofluorescence assay, comprising:
   a. providing a mixture of cells to be analyzed and synthetic calibration particles, whereby the cells and particles are fixed to a solid phase,
   b. detecting the synthetic calibration particles, followed by calibrating and focusing of a fluorescent microscopy device and an automated evaluation system based on said detecting of the synthetic calibration particles,
   c. incubating said mixture with one or more antibodies that bind to a target substrate of the cells,
   d. detecting the antibodies bound to said substrates via said fluorescent microscopy device, and
   e. determining immunofluorescent foci from image data generated by said fluorescent microscopy device using said automated evaluation system.

2. Method according to claim 1, wherein said immunofluorescent foci are gamma H2Ax foci.

3. Method according to claim 1, wherein said synthetic calibration particles are microparticles.

4. Method according to claim 1, wherein said synthetic calibration particles and/or antibodies are specifically marked using fluorescent markers.

5. Method according to claim 1, wherein said one or more antibodies are one or more primary antibodies that bind to the target substrate of the cell, and one or more secondary antibody that is fluorescently marked and binds to the primary antibody, thereby facilitating detection of the bound substrate as immunofluorescent foci.

6. Method according to claim 1, wherein said cells are selected from the group consisting of mononuclear blood cells, in-vitro cultured cells, and cells from an experimental cell line.

7. Method according to claim 1, wherein said calibrating in step b) or said determining in step e) comprises detecting and locating of cells via detection of stained or marked cell nuclei.

8. Method according to claim 7, wherein said determining provides a determination of foci number per cell.

9. Method according to claim 1, wherein said automated evaluation system of step b) comprises a computing device with a computer readable memory storing executable instructions as software, comprising modules that, when executed by the computer, perform functions of autofocus control, automated image acquisition, automated image analysis and/or automated pattern recognition.

10. Method according to claim 1, wherein the focusing of the fluorescent microscopy and automated evaluation system occurs via dynamic auto-focusing of the microscopic image.

11. A method of determining the number of DNA double strand breaks in a cell and/or cell population comprising performing the method of claim 2, wherein the number of gamma H2Ax foci is proportional to the number of DNA double strand breaks.

12. The method according to claim 11, wherein
   a. the number of gamma H2Ax foci in test cells is compared to the number of gamma H2Ax foci in control cells, and
   b. a larger number of gamma H2Ax foci per cell in the test cells in comparison to control cells indicates increased DNA damage in the test cells.

13. A method for determining radiation exposure of a cell and/or cell population to ionizing or any other kind of radiation, or any other DNA-damaging substance or treatment comprising performing the method of claim 1, wherein the number of immunofluorescent foci determined indicates a degree of radiation exposure or exposure to said DNA-damaging substance or treatment.

14. System for the automated determination of immunofluorescent foci by an immunofluorescence assay according to the method of claim 1, comprising
   a. a mixture of cells to be analyzed and synthetic calibration particles, wherein the cells and the particles are fixed to a solid phase
   b. a fluorescent microscopy device comprising a fluorescent microscope with a camera, a motorized scanning stage and multichannel light-emitting diodes (LED), and
   c. an automated evaluation system comprising a computing device with a computer readable memory storing executable instructions as software, comprising modules that, when executed by the computer, perform functions of autofocus control, automated image acquisition, automated image analysis and/or automated pattern recognition,
whereby two or more color channels are analyzed, each corresponding to either synthetic calibration particles or target substrate-associated immunofluorescent foci.

15. Kit for carrying out a method for automated determination of immunofluorescent foci by an immunofluorescence assay according to claim 1, comprising
   a. one or more solid phases comprising synthetic calibration particles fixed to the surface of said solid phase, upon which the cells to be analyzed are to be fixed,
   b. one or more conjugates comprising an immunoglobulin-specific antibody conjugated with a fluorescent label, and optionally
   c. wash buffer, cover slips, covering medium, and/or fluorescent labels for the synthetic calibration particles, primary antibody and/or secondary antibody.

16. The method according to claim 3, wherein the microparticles are between 1-100 μm in diameter.

17. The method according to claim 6, wherein the mononuclear blood cells are lymphocytes, monocytes and/or macrophages.

18. The method according to claim 6, wherein the in-vitro cultured cells are fibroblasts.

19. The method of claim 7, wherein said detecting and locating of cells is done by detection of DAPI-stained cell nuclei.

20. The kit of claim 15, wherein said one or more conjugates comprising an immunoglobulin-specific antibody conjugated with a fluorescent label is/are configured for use as a secondary antibody(ies).

* * * * *